US010492767B2

United States Patent
Halmann et al.

(10) Patent No.: US 10,492,767 B2
(45) Date of Patent: Dec. 3, 2019

(54) METHOD AND SYSTEM FOR SEQUENTIAL NEEDLE RECALIBRATION

(71) Applicant: General Electric Company, Schenectady, NY (US)

(72) Inventors: Menachem Halmann, Wauwatosa, WI (US); David J. Bates, Wauwatosa, WI (US); Jeffery Scott Peiffer, Wauwatosa, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 592 days.

(21) Appl. No.: 14/159,174

(22) Filed: Jan. 20, 2014

(65) Prior Publication Data

US 2015/0201911 A1   Jul. 23, 2015

(51) Int. Cl.
*A61B 8/00* (2006.01)
*A61B 8/08* (2006.01)
*A61B 8/13* (2006.01)
*A61B 10/04* (2006.01)

(52) U.S. Cl.
CPC .............. *A61B 8/58* (2013.01); *A61B 8/0841* (2013.01); *A61B 8/13* (2013.01); *A61B 8/4254* (2013.01); *A61B 8/5207* (2013.01); *A61B 10/04* (2013.01); *A61B 2010/045* (2013.01)

(58) Field of Classification Search
CPC combination set(s) only.
See application file for complete search history.

(56) References Cited

U.S. PATENT DOCUMENTS

| 5,538,004 A | * | 7/1996 | Bamber | G01S 7/52044 128/916 |
| 6,484,118 B1 | * | 11/2002 | Govari | A61B 5/06 702/150 |
| 6,524,247 B2 | | 2/2003 | Zhao et al. | |

(Continued)

FOREIGN PATENT DOCUMENTS

WO       2013034175 A1    3/2013

OTHER PUBLICATIONS

International Search Report and Written Opinion regarding International Application No. PCT/US2015/011980, dated Apr. 1, 2015, 9 pages.

*Primary Examiner* — James M Kish
(74) *Attorney, Agent, or Firm* — McAndrews, Held & Malloy, Ltd.; Jacob Groethe; David Bates

(57) ABSTRACT

Various embodiments include a system and method that provide sequential needle recalibration by correlating a sequence of calibration data for a tracking system to a plurality of corresponding ultrasound probe positions during a calibration sequence such that the appropriate calibration data is retrieved and applied based on the position of the ultrasound probe during a procedure. The method can include acquiring a sequence of calibration data for a tracking system at a plurality of different ultrasound probe positions. The sequence of calibration data may be acquired from a tracking sensor attached to or within the ultrasound probe. The tracking system can include the tracking sensor and a tracking emitter attached to or within a surgical instrument. The method may include generating, by a processor of the ultrasound system, an index correlating each of the sequence of calibration data to a corresponding one of the plurality of different ultrasound probe positions.

19 Claims, 2 Drawing Sheets

(56) References Cited

U.S. PATENT DOCUMENTS

| | | |
|---|---|---|
| 2007/0055468 A1 | 3/2007 | Pylvanainen |
| 2011/0237949 A1* | 9/2011 | Zhao .................. A61B 8/488 |
| | | 600/443 |
| 2011/0282188 A1 | 11/2011 | Burnside et al. |
| 2011/0295108 A1 | 12/2011 | Cox et al. |
| 2012/0143029 A1 | 6/2012 | Silverstein et al. |
| 2014/0257080 A1 | 9/2014 | Dunbar et al. |
| 2014/0257746 A1* | 9/2014 | Dunbar .................. G01B 7/003 |
| | | 702/150 |

* cited by examiner

METHOD AND SYSTEM FOR SEQUENTIAL NEEDLE RECALIBRATION

CROSS-REFERENCE TO RELATED APPLICATIONS/INCORPORATION BY REFERENCE

[Not Applicable]

FIELD OF THE INVENTION

Certain embodiments of the invention relate to ultrasound imaging and surgical instrument tracking and calibration. More specifically, certain embodiments of the invention relate to a method and system for sequential needle recalibration by correlating a sequence of calibration data for a tracking system to a plurality of corresponding ultrasound probe positions during a calibration sequence such that the appropriate calibration data is retrieved and applied based on the position of the ultrasound probe during a procedure.

BACKGROUND OF THE INVENTION

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Ultrasound imaging system operators often rely upon technology when performing a medical procedure, such as a biopsy procedure. A tracking system may provide positioning information for the needle with respect to the patient, a reference coordinate system, or the ultrasound probe, for example. An operator may refer to the tracking system to ascertain the position of the needle even when the needle is not within the region or volume of tissue currently being imaged and displayed. As such, the tracking or navigation system allows the operator to visualize the patient's anatomy and better track the position and orientation of the needle. The operator may use the tracking system to determine when the needle is positioned in a desired location such that the operator may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

Tracking systems may be electromagnetic or optical tracking systems, for example. Electromagnetic tracking systems may employ a permanent magnet as an emitter and a sensor as a receiver, or can employ coils as receivers and transmitters. Magnetic fields generated by the permanent magnet(s) or transmitter coil(s) may be detected by the sensor(s) or receiver coil(s) and used to determine position and orientation information of a surgical instrument, for example. Prior to performing a medical procedure, the tracking system is calibrated. For example, in a tracking system comprising a permanent magnet emitter coupled to or within a surgical needle and one or more sensors coupled to or within a probe, the needle may be removed from the surgical environment so that the tracking system can be calibrated while the probe is held stationary to remove or zero-out ambient magnetic fields detected by the sensor(s). However, even a slight subsequent movement (e.g., a tilt or a rotation relative to the calibration position or orientation) of the hand-held ultrasound probe during a procedure can cause positioning errors in the tracking system, which may necessitate recalibration of the tracking system. In known tracking systems that use permanent magnets, for example, recalibration is typically performed by removing the surgical instrument that includes the emitter from the surgical environment, which could be inconvenient when the surgical instrument is within a patient, for example, and then holding the probe stationary during recalibration.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for sequential needle recalibration, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Figure 1:
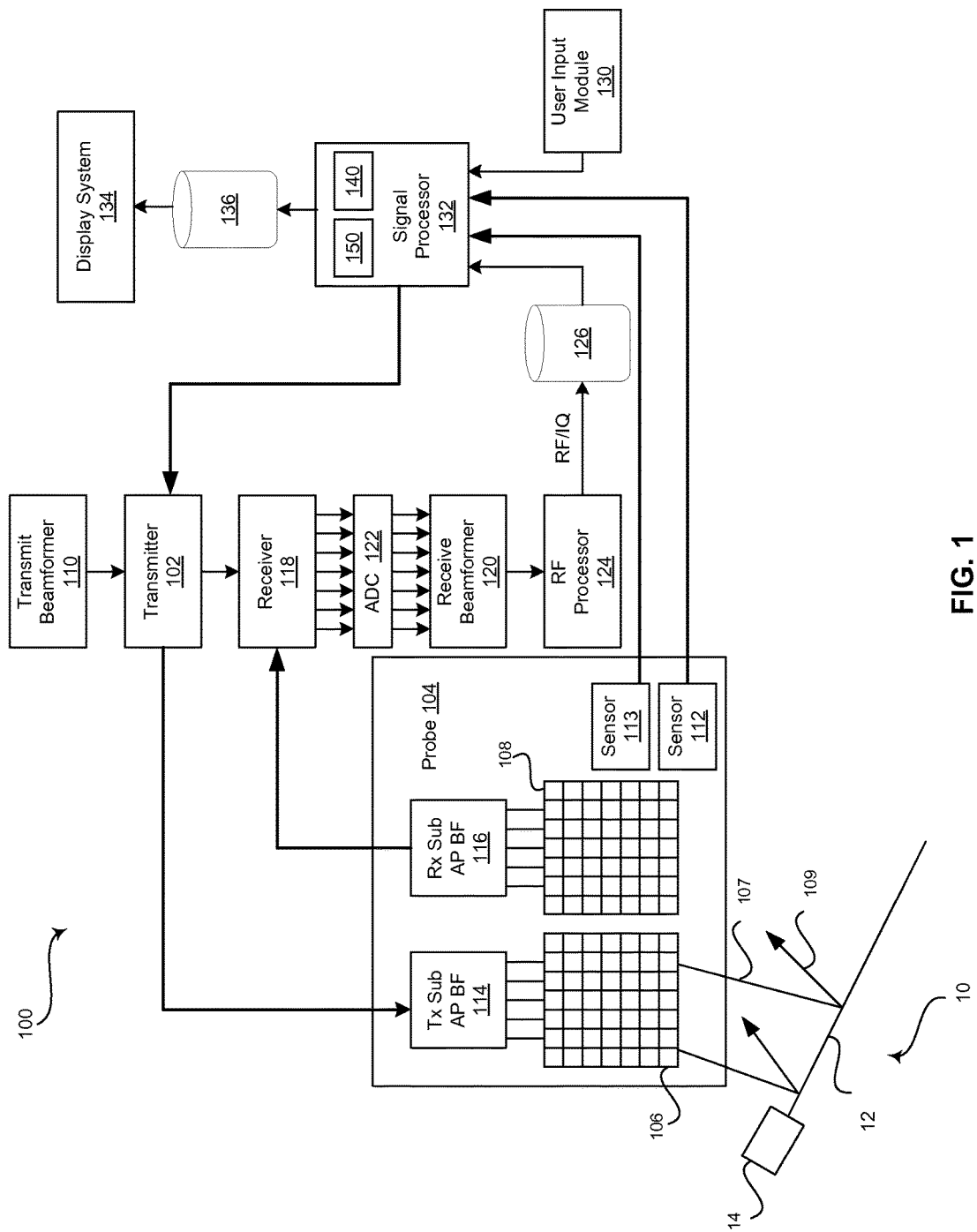
FIG. 1 is a block diagram of an exemplary ultrasound system that is operable to provide sequential needle recalibration by correlating a sequence of calibration data for a tracking system to a plurality of corresponding ultrasound probe positions, in accordance with an embodiment of the invention.

Certain embodiments of the invention may be found in a method and system for providing sequential needle recalibration by correlating a sequence of calibration data for a tracking system to a plurality of corresponding ultrasound probe positions during a calibration sequence such that the appropriate calibration data is subsequently retrieved and applied based on the position of the ultrasound probe during a procedure.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to provide sequential needle recalibration by correlating a sequence of calibration data for a tracking system 112, 14 (and optionally 113) to a plurality of corresponding ultrasound probe positions, in accordance with an embodiment of the invention. Referring to FIG. 1, there is shown a surgical instrument 10 and an ultrasound system 100. The surgical instrument 10 can be a surgical needle that comprises a needle portion 12 and a needle emitter 14. Notwithstanding, the invention is not limited in this regard. Accordingly, in some embodiments of the invention, the surgical instrument may be any suitable surgical instrument. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, and a display system 134.

The surgical needle 10 comprises a needle portion 12 that includes a distal insertion end and a proximal hub end. A needle emitter 14 is attached to the needle portion 12 at the proximal hub end and/or is secured within a housing attached to the proximal hub end of the needle portion 12. The needle emitter 14 can correspond with a probe sensor 112 of the ultrasound system 100 probe 104, for example. The emitter may be a permanent magnet that corresponds with a sensor, an electromagnetic coil that corresponds with a receiver, an optical source that corresponds with a photo-detector, or any suitable emitter that corresponds with a sensor to form a tracking system. As an example, the needle emitter 14 may comprise a magnetic element that generates a magnetic field detectable by one or more sensors of the probe sensor 112 to enable the position and orientation of the surgical needle 10 to be tracked relative to the probe 104 by the ultrasound system 100.

The transmitter 102 may comprise suitable logic, circuitry, interfaces and/or code that may be operable to drive an ultrasound probe 104. The ultrasound probe 104 may comprise suitable logic, circuitry, interfaces and/or code, which may be operable to perform some degree of beam steering, which may be within a particular scan plane (e.g., B-slice) as well as perpendicular to the scan plane direction (i.e., in the elevation direction). The ultrasound probe 104 may comprise a two dimensional (2D) or three dimensional (3D) array of piezoelectric elements. In an exemplary embodiment of the invention, the ultrasound probe 104 may comprise a three dimensional (3D) array of elements that is operable through suitable delays to steer a beam in the desired spatial 3D direction with a desired depth of focus to repeatedly acquire and display a volume of interest in substantially real-time or, alternatively or in addition, a scan plane within such volume. Alternatively, the probe 104 may comprise a 2D array that performs electronic steering in the azimuth direction and mechanical oscillation in the elevation direction to acquire a 3D volume in substantially real-time.

Regardless whether the ultrasound probe 104 is capable of 2D operation only or 3D operation as well, it may comprise a group of transmit transducer elements 106 and a group of receive transducer elements 108, that normally constitute the same elements. The ultrasound probe 104 may comprise a sensor 112 for coordinating with a needle emitter 14 to track the position and/or orientation of a surgical needle 10 with respect to the probe 104. The sensor 112 can correspond with a permanent magnet, an electromagnetic coil, an optical source, or any suitable emitter 14 associated with (e.g., attached to) the needle 10 to form a tracking system. In various embodiments, the ultrasound probe 104 may comprise a probe sensor 113 comprising suitable logic, circuitry, interfaces and/or code that may be operable to provide probe position and/or orientation information. The sensor 113 may include an accelerometer, such as a three-axis accelerometer or any suitable sensor device operable to provide data related to the position and/or orientation (and/or relative changes in position and/or orientation) of the ultrasound probe 104, for example.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals 107 into a 2D or 3D region of interest (e.g., human, animal, underground cavity, physical structure and the like). The transmitted ultrasonic signals 107 may be back-scattered from structures in the object of interest, like blood cells or tissue, as well as any surgical instruments in the region or object of interest, like a surgical needle 10, to produce echoes 109. The echoes 109 are received by the receive transducer elements 108.

The group of receive transducer elements 108 in the ultrasound probe 104 may be operable to convert the received echoes 109 into analog signals, undergo sub-aperture beamforming by a receive sub-aperture beamformer 116, and are then communicated to a receiver 118. As noted above, the receive elements 108 may be the same physical structures as the transmit transducer elements 106 but separately controlled for transmitting and receiving operations via a suitable Tx/Rx switch (not shown).

The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122.

The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the invention is not limited in this regard. Accordingly, in some embodiments of the invention, the plurality of A/D converters 122 may be integrated within the receiver 118.

The receive beamformer 120 may comprise suitable logic, circuitry, interfaces and/or code that may be operable to perform digital beamforming processing on the signals received from the plurality of A/D converters 122. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment of the invention, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126 as well as to a more permanent memory (not shown) for storage, such as a hard disk for example.

The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, surgical instrument data, scan parameters, settings, configuration parameters, change scan mode, and the like. In an exemplary embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, and/or the display system 134.

The signal processor 132 may comprise suitable logic, circuitry, interfaces and/or code that may be operable to process ultrasound scan data (i.e., RF signal data or IQ data pairs) for generating an ultrasound image for presentation on a display system 134. The signal processor 132 is operable to perform one or more processing operations according to a plurality of selectable ultrasound modalities on the acquired ultrasound scan data. In an exemplary embodiment of the invention, the signal processor 132 may be operable to perform compounding, motion tracking, and/or speckle tracking. Acquired ultrasound scan data may be processed and displayed in real-time during a scanning session as the echo signals 109 are received. Additionally or alternatively, the ultrasound scan data may be stored temporarily in the RF/IQ buffer 126 or some less transitory memory (not shown) during a scanning session and processed in less than real-time in a live or off-line operation.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds worth of frames of ultrasound scan data. The frames of ultrasound scan data are stored in a manner to facilitate retrieval thereof according to its order or time of acquisition. The image buffer 136 may be embodied as any known data storage medium. The processed images may also be stored in a less transitory memory (not shown) for later retrieval and display, such as a hard drive, for example.

The signal processor 132 may comprise suitable logic, circuitry, interfaces and/or code that may be operable to correlate a sequence of acquired calibration data for a tracking system 112, 14 (and optionally 113) to a plurality of corresponding ultrasound probe 104 positions during a calibration sequence and apply the appropriate calibration data to the tracking system 112, 14 (and optionally 113) based on the position and/or movement of the ultrasound probe 104 during a procedure. In the exemplary embodiment, the signal processor 132 may comprise a calibration module 140.

The calibration module 140 may comprise suitable logic, circuitry, interfaces and/or code that may be operable to acquire a sequence of calibration data for a tracking system at a plurality of different ultrasound probe positions. For example, the calibration module 140 can acquire data detected by the sensor(s) 112 for removing or zeroing-out ambient magnetic fields. The calibration data may be acquired sequentially at a plurality of different ultrasound probe positions. For example, the ultrasound probe 104 can be tilted forward, tilted back, tilted left, tilted right, and/or rotated while the calibration data is sequentially acquired by sensor(s) 112. In various embodiments, the ultrasound probe positions may be provided to the calibration module 140 by a sensor 113 attached to and/or integrated with the ultrasound probe 104. The sensor 113 can include an accelerometer or any suitable sensor device operable to provide data related to the position and/or orientation and/or movement of the ultrasound probe 104. Additionally and/or alternatively, the ultrasound probe positions can be determined by the calibration module based on images acquired by the ultrasound probe 104 during the calibration sequence. When the probe 104 is acquiring 3D volumes, cross-correlation between the volumes may be used to precisely detect probe movement and rotation (thus obviating the need for the separate sensor 113) in order to identify which set of calibration data to use.

Regardless of how probe movement is detected, the calibration module can comprise suitable logic, circuitry, interfaces and/or code that may be operable to generate an index correlating each of the acquired calibration data in the sequence to the corresponding different ultrasound probe position. During a subsequent procedure, the calibration module 140 may retrieve the previously acquired calibration data from the index based on a current ultrasound probe position and apply the retrieved calibration data to the tracking system 112, 14 (and optionally 113), for example.

The signal processor 132 may comprise suitable logic, circuitry, interfaces and/or code that may be operable to process acquired tracking information (i.e., magnetic field strength data or any suitable tracking information from sensor 112 and optionally probe movement information from sensor 113) and determine a position and orientation of a surgical instrument 10 relative to the probe 104 as well as movement of the probe 104. In the exemplary embodiment, the signal processor 132 may comprise a tracking module 150.

To reduce the number of calibration data sets that are acquired and stored, while still ensuring suitable calibration data is available during a procedure to compensate for any unintended or intended movements probe 104, it may be desirable to acquire a relatively small set of calibration data during the initial calibration sequence (i.e., when the needle 10 is removed from the immediate vicinity so the local magnetic field strength and orientation can be sensed prior to beginning the clinical procedure). Then, when the position or a particular movement of the probe 104 is identified during a clinical procedure, signal processor 132 may interpolate two or more previously acquired calibration sets to obtain an accurate calibration data. For example, the system 100 may acquire 5 calibration data sets while the probe is rotated during an initial calibration procedure. The system 100 would then identify the probe location (i.e., orientation and position) at which each calibration set was acquired (based on the previously described methods). During a subsequent clinical scanning operation, when a specific probe location is identified that does not precisely match a corresponding probe location associated with stored calibration data, the current calibration data may be interpolated from those 5 data sets.

The tracking module 150 may comprise suitable logic, circuitry, interfaces and/or code that may be operable to handle processing and application of tracking data. For example, the tracking module 150 can comprise suitable logic, circuitry, interfaces and/or code that may be operable to provide a representation of a surgical instrument 10 to overlay on ultrasound image data, determine an ultrasound beam steering angle for enhancing the visualization of a surgical instrument, calculating a tracking system and/or ultrasound system calibration error, or any suitable purpose.

Figure 2:
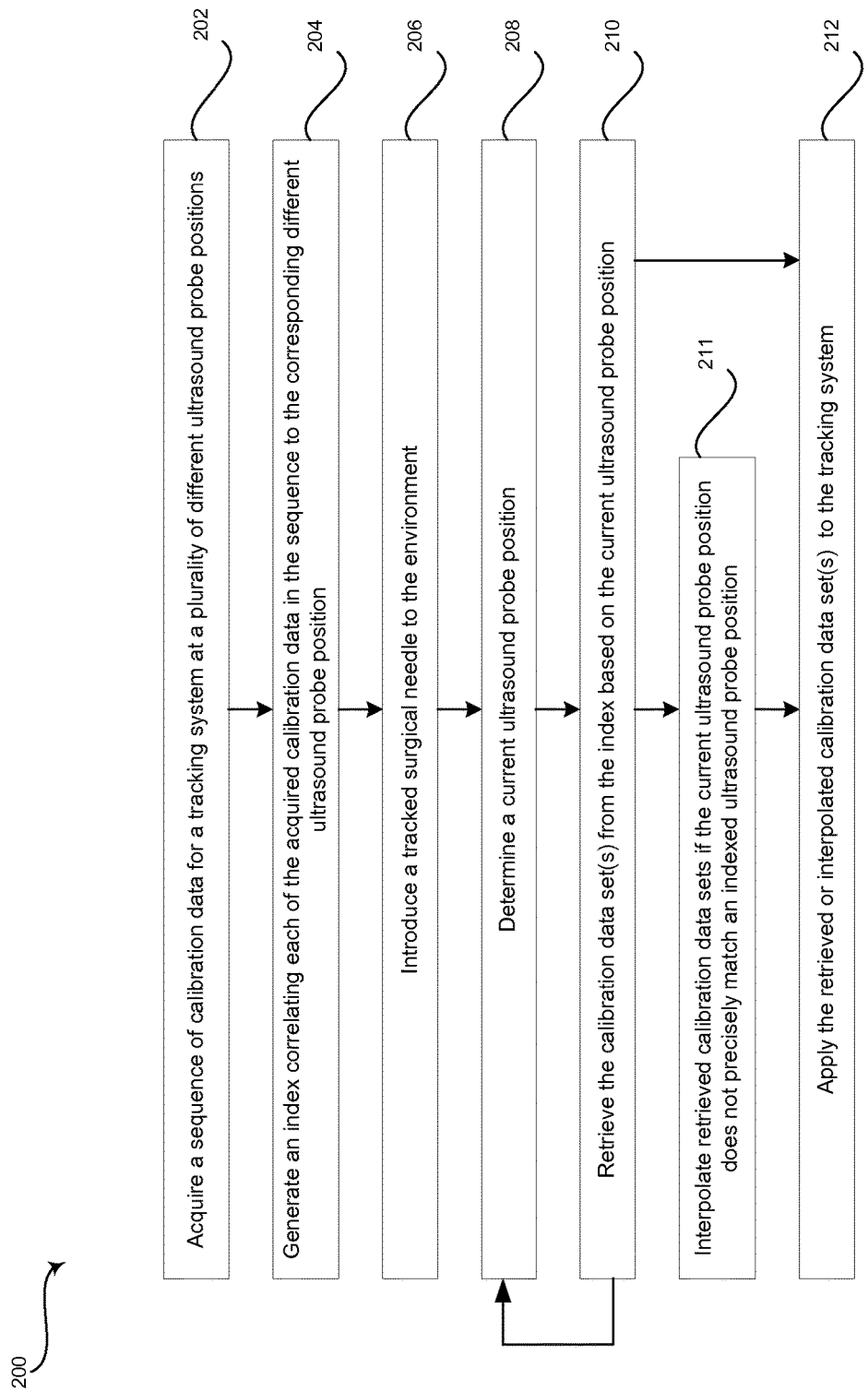
FIG. 2 is a flow chart illustrating exemplary steps that may be utilized for providing sequential needle recalibration by correlating a sequence of calibration data for a tracking system to a plurality of corresponding ultrasound probe positions, in accordance with an embodiment of the invention.

FIG. 2 is a flow chart illustrating exemplary steps that may be utilized for providing sequential needle recalibration by correlating a sequence of calibration data for a tracking system 112, 14 (and optionally 113) to a plurality of corresponding ultrasound probe 104 positions, in accordance with an embodiment of the invention. Referring to FIG. 2, there is shown a flow chart 200 comprising exemplary steps 202 through 212. Certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

In step 202, a calibration module 140 of a signal processor 132 in the ultrasound system 100 may be operable to acquire a sequence of calibration data for a tracking system 112, 14 (and optionally 113) at a plurality of different ultrasound probe positions. For example, in a tracking system comprising a permanent magnet emitter 14 coupled to or within a surgical needle 10 and one or more sensors 112 (and optionally 113) coupled to or within a probe 104, the needle 10 may be removed from the surgical environment so that the tracking system can be calibrated to remove or zero-out ambient magnetic fields detected by the sensor(s) 112 (and optionally associated with readings from sensor 113). The sequence of calibration data can be detected by sensor(s) 112 (and optionally 113) and communicated to the processor 132, 140. The ultrasound probe positions may be provided to the processor 132, 140 by a sensor 113 attached to and/or integrated with the ultrasound probe 104. Additionally and/or alternatively, the ultrasound probe positions can be determined by the processor 132, 140 based on cross-correlation of 2D and especially 3D images acquired by the ultrasound probe 104 during the calibration sequence 202. The plurality of different ultrasound probe position can correspond with the ultrasound probe 104 being tilted forward, tilted back, tilted left, tilted right, and/or rotated while the calibration data is sequentially acquired by sensor(s) 112 (and optionally 113).

In step 204, the calibration module 140 of the signal processor 132 in the ultrasound system 100 can be operable to generate an index correlating each of the acquired calibration data to the corresponding different ultrasound probe position. The index can be a look-up table or any suitable data structure that associates ultrasound probe position and/or orientation information with calibration data. In various embodiments, the ultrasound probe position and/or orientation information can be data from a sensor 113, such as an accelerometer or any suitable sensor device, attached to and/or integrated with the ultrasound probe 104. Additionally and/or alternatively, the ultrasound probe position and/or orientation information can be an image acquired by the ultrasound probe 104 or data extracted from an image acquired by the ultrasound probe 104, for example.

In step 206, a surgical needle 10 can be introduced to the surgical environment. For example, once the tracking system 112, 14 (and optionally 113) is calibrated, an operator may begin a procedure.

In step 208, the calibration module 140 of the signal processor 132 may determine a current ultrasound probe position. For example, the calibration module 140 of the signal processor 132 can determine a current ultrasound probe position or movement based on data provided by a sensor 113 attached to and/or integrated with the ultrasound probe 104 provided to the processor 132, 140. Additionally and/or alternatively, a current ultrasound probe position may correspond with images acquired by the ultrasound probe 104 during the surgical procedure.

In step 210, the calibration module 140 of the signal processor 132 can retrieve one or more calibration data sets from the index generated at step 204 based on the current ultrasound probe position determined in step 208. For example, the data provided by sensor 113 may be used to lookup calibration data in the index that corresponds with an ultrasound probe position closest to the current ultrasound probe position. As another example, images acquired during the surgical procedure can be used to lookup calibration data in the index by comparing the images acquired during the surgical procedure with images (including 3D volumes) acquired during the calibration sequence to identify calibration data that corresponds with an ultrasound probe position closest to the current ultrasound probe position. In various embodiments, the images acquired during the surgical procedure may be compared to images acquired during the calibration sequence based on cross-correlation techniques such as pattern matching, speckle tracking, or any suitable image data comparison procedure.

If the current ultrasound probe position detected at step 208 does not precisely match an indexed ultrasound probe position, multiple sets of calibration data can be retrieved in step 210 and interpolated in step 211. For example, to reduce the number of calibration data sets that are acquired and stored, while still ensuring suitable calibration data is available during a procedure to compensate for any unintended or intended movements of the probe 104, a relatively small number of sets of calibration data can be acquired at step 202. Then, when the position or a particular movement of the probe 104 is identified during a clinical procedure at step 208, the calibration module 140 of the signal processor 132 may interpolate two or more previously acquired calibration sets to generate accurate calibration data.

In step 212, the calibration module 140 of the signal processor 132 can apply the retrieved or interpolated calibration data set(s) to the tracking system 112, 14 (and optionally 113). For example, the retrieved calibration data can be applied to the tracking system 112, 14 (and optionally 113) to remove or zero-out ambient magnetic fields detected by the sensor(s) 112.

Aspects of the present invention have the technical effect of providing sequential needle recalibration by correlating a sequence of calibration data for a tracking system 112, 14 (and optionally 113) to a plurality of corresponding ultrasound probe positions during a calibration sequence such that the appropriate calibration data is retrieved and applied based on the position of the ultrasound probe 104 during a procedure. In accordance with various embodiments of the invention, a method 200 comprises acquiring 202, from a tracking sensor 112 attached to or within an ultrasound probe 104 of an ultrasound system 100, a sequence of calibration data for a tracking system 112, 14 (and optionally 113) at a plurality of different ultrasound probe positions. The tracking system 112, 14 (and optionally 113) comprises the tracking sensor 112 and a tracking emitter 14 attached to or within a surgical instrument 10, and may also comprise a probe movement sensor 113. The method 200 comprises generating 204, by a processor 140, 132 of the ultrasound system 100, an index correlating each of the sequence of calibration data to a corresponding one of the plurality of different ultrasound probe positions.

In a representative embodiment, the method 200 comprises determining 208 a current ultrasound probe 104 position after the sequence of calibration data is acquired 202 and the index is generated 204. In various embodiments, the method 200 comprises retrieving 210 one of the sequence of calibration data based on the index and the determined current ultrasound probe position. In certain embodiments, the method 200 comprises applying 212 the retrieved one of the sequence of calibration data to the tracking system 112, 14 (and optionally 113). In a representative embodiment, one or more of the current ultrasound probe position and the plurality of different ultrasound probe positions is acquired from a probe sensor 113 attached to or within the ultrasound probe 104 of the ultrasound system 100. In various embodiments, the probe sensor 113 is a three-axis accelerometer.

In certain embodiments, the current ultrasound probe position and each of the plurality of different ultrasound probe positions is represented by a 2D or 3D image acquired by the ultrasound probe 104. In a representative embodiment, the retrieving 210 one of the sequence of calibration data based on the determined current ultrasound probe position comprises comparing the image representing the current ultrasound probe position with each of the images representing the plurality of different ultrasound positions to identify a closest match or matches. In various embodiments, the comparing the image representing the current ultrasound probe position with each of the images representing the plurality of different ultrasound positions is performed by at least one of speckle tracking and pattern matching.

In a representative embodiment, the method 200 comprises interpolating 211 the identified closest matches to generate the retrieved one of the sequence of calibration data. In certain embodiments, the retrieving 210 one of the sequence of calibration data comprises interpolating 211 a plurality of the sequence of calibration data associated with the plurality of different ultrasound positions representing closest matches with the determined current ultrasound probe position.

Various embodiments provide a system comprising a tracking system 112, 14 (and optionally 113) and an ultrasound device 100. The tracking system 112, 14 comprises a tracking sensor 112 and a tracking emitter 14, and it may also include a probe movement sensor 113. The tracking sensor 112 (and optional probe sensor 113) is (are) attached to or within an ultrasound probe 104 of the ultrasound device 100. The tracking emitter 14 is attached to or within a surgical instrument 10. The ultrasound device comprises a processor 140, 132. The processor 140, 132 is operable to acquire, from the tracking sensor 112 (and optionally 113), a sequence of calibration data for the tracking system 112, 14 (and optionally 113) at a plurality of different ultrasound probe positions. The processor 140, 132 is operable to generate an index correlating each of the sequence of calibration data to a corresponding one of the plurality of different ultrasound probe positions.

In certain embodiments, the processor 140, 132 is operable to determine a current ultrasound probe position after the sequence of calibration data is acquired and the index is generated. In various embodiments, the processor 140, 132 is operable to retrieve one of the sequence of calibration data based on the index and the determined current ultrasound probe position. In a representative embodiment, the processor 140, 132 is operable to apply the retrieved (or interpolated) one of the sequence of calibration data to the tracking system 112, 14 (and optionally 113).

In various embodiments, at least one of the current ultrasound probe position and the plurality of different ultrasound probe positions is acquired from a probe sensor 113 attached to or within the ultrasound probe 104 of the ultrasound device 100. In certain embodiments, the current ultrasound probe position and each of the plurality of different ultrasound probe positions is represented by a 2D or 3D image acquired by the ultrasound probe 104. In a representative embodiment, the processor 140, 132 is operable to compare the image representing the current ultrasound probe position with each of the images representing the plurality of different ultrasound positions to determine which one of the sequence of calibration data to retrieve based on an identified closest match or matches. In various embodiments, the processor 140, 132 is operable to interpolate the identified closest matches to generate the retrieved one of the sequence of calibration data. In certain embodiments, the processor 140, 132 is operable to interpolate a plurality of the sequence of calibration data associated with the plurality of different ultrasound positions representing closest matches with the determined current ultrasound probe position to generate the retrieved one of the sequence of calibration data.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing sequential needle recalibration by correlating a sequence of calibration data for a tracking system to a plurality of corresponding ultrasound probe positions.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method, comprising:

acquiring, from a tracking sensor attached to or within an ultrasound probe of an ultrasound system, a sequence of calibration data sets for a tracking system at a plurality of different ultrasound probe positions, the tracking system comprising the tracking sensor and a tracking emitter attached to or within a surgical instrument, the tracking emitter operable to generate a magnetic field detectable by the tracking sensor for determining one or both of a position and orientation of the surgical instrument relative to the ultrasound probe, the sequence of calibration data sets comprising data for removing ambient magnetic fields;

generating, by a processor of the ultrasound system, an index correlating each of the calibration data sets in the sequence of calibration data sets to a corresponding one of the plurality of different ultrasound probe positions;

determining, by the processor, a current ultrasound probe position after the sequence of calibration data sets is acquired and the index is generated;

retrieving, by the processor, one of the calibration data sets in the sequence of calibration data sets based on the index and the determined current ultrasound probe position; and applying, by the processor, the retrieved one of the calibration data sets in the sequence of calibration data sets to the tracking system to remove the ambient magnetic fields.

2. The method according to claim 1, wherein at least one of the current ultrasound probe position and the plurality of different ultrasound probe positions is acquired from a probe sensor, different from the tracking sensor, attached to or within the ultrasound probe of the ultrasound system.

3. The method according to claim 2, wherein the probe sensor is a three-axis accelerometer.

4. The method of according to claim 2, wherein the retrieving one of the calibration data sets in the sequence of calibration data sets comprises interpolating a plurality of the calibration data sets in the sequence of calibration data sets associated with the plurality of different ultrasound positions representing closest matches with the determined current ultrasound probe position.

5. The method according to claim 1, wherein the current ultrasound probe position and each of the plurality of different ultrasound probe positions is represented by a 2D or 3D image acquired by the ultrasound probe.

6. The method according to claim 5, wherein the retrieving one of the calibration data sets in the sequence of calibration data sets based on the determined current ultrasound probe position comprises comparing the image representing the current ultrasound probe position with each of the images representing the plurality of different ultrasound positions to identify a closest match or matches.

7. The method according to claim 6, wherein the comparing the image representing the current ultrasound probe position with each of the images representing the plurality of different ultrasound positions is performed by at least one of speckle tracking and pattern matching.

8. The method according to claim 6, comprising interpolating the identified closest matches to generate the retrieved one of the calibration data sets in the sequence of calibration data sets.

9. A system, comprising:
a tracking system comprising a tracking sensor and a tracking emitter, the tracking emitter attached to or within a surgical instrument, the tracking emitter operable to generate a magnetic field detectable by the tracking sensor for determining one or both of a position and orientation of the surgical instrument relative to an ultrasound probe; and
an ultrasound device comprising:
  a processor operable to:
    acquire, from the tracking sensor attached to or within the ultrasound probe of the ultrasound device, a sequence of calibration data sets for the tracking system at a plurality of different ultrasound probe positions, the sequence of calibration data sets comprising data for removing ambient magnetic fields,
    generate an index correlating each of the calibration data sets in the sequence of calibration data sets to a corresponding one of the plurality of different ultrasound probe positions,
    determine a current ultrasound probe position after the sequence of calibration data sets is acquired and the index is generated,
    retrieve one of the calibration data sets in the sequence of calibration data sets based on the index and the determined current ultrasound probe position, and
    apply the retrieved one of the calibration data sets in the sequence of calibration data sets to the tracking system to remove the ambient magnetic fields.

10. The system according to claim 9, wherein at least one of the current ultrasound probe position and the plurality of different ultrasound probe positions is acquired from a probe sensor, different from the tracking sensor, attached to or within the ultrasound probe of the ultrasound device.

11. The system according to claim 10, wherein the processor is operable to interpolate a plurality of the calibration data sets in the sequence of calibration data sets associated with the plurality of different ultrasound positions representing closest matches with the determined current ultrasound probe position to generate the retrieved one of the calibration data sets in the sequence of calibration data sets.

12. The system according to claim 9, wherein the current ultrasound probe position and each of the plurality of different ultrasound probe positions is represented by a 2D or 3D image acquired by the ultrasound probe.

13. The system according to claim 12, wherein the processor is operable to compare the image representing the current ultrasound probe position with each of the images representing the plurality of different ultrasound positions to determine which one of the calibration data sets in the sequence of calibration data sets to retrieve based on an identified closest match or matches.

14. The system according to claim 13, wherein the processor is operable to interpolate the identified closest matches to generate the retrieved one of the calibration data sets in the sequence of calibration data sets.

15. A non-transitory computer readable medium having stored thereon, a computer program having at least one code section, the at least one code section being executable by a machine for causing the machine to perform steps comprising:
acquiring, from a tracking sensor attached to or within an ultrasound probe of an ultrasound system, a sequence of calibration data sets for a tracking system at a plurality of different ultrasound probe positions, the tracking system comprising the tracking sensor and a tracking emitter attached to or within a surgical instrument, the tracking emitter operable to generate a magnetic field detectable by the tracking sensor for determining one or both of a position and orientation of the surgical instrument relative to the ultrasound probe, the sequence of calibration data sets comprising data for removing ambient magnetic fields;
generating an index correlating each of the calibration data sets in the sequence of calibration data sets to a corresponding one of the plurality of different ultrasound probe positions;
determining a current ultrasound probe position after the sequence of calibration data sets is acquired and the index is generated;
retrieving one of the calibration data sets in the sequence of calibration data sets based on the index and the determined current ultrasound probe position; and
applying the retrieved one of the calibration data sets in the sequence of calibration data sets to the tracking system to remove the ambient magnetic fields.

16. The non-transitory computer readable medium according to claim 15, wherein at least one of the current ultrasound probe position and the plurality of different ultrasound probe positions is acquired from a probe sensor, different from the tracking sensor, attached to or within the ultrasound probe of the ultrasound system.

17. The non-transitory computer readable medium according to claim 16, wherein the retrieving one of the calibration data sets in the sequence of calibration data sets comprises interpolating a plurality of the calibration data sets in the sequence of calibration data sets associated with the plurality of different ultrasound positions representing closest matches with the determined current ultrasound probe position.

18. The non-transitory computer readable medium according to claim 15, wherein:
the current ultrasound probe position and each of the plurality of different ultrasound probe positions is represented by a 2D or 3D image acquired by the ultrasound probe, and
the retrieving one of the calibration data sets in the sequence of calibration data sets based on the determined current ultrasound probe position comprises comparing the image representing the current ultrasound probe position with each of the images representing the plurality of different ultrasound positions to identify a closest match or matches.

19. The non-transitory computer readable medium according to claim 18, comprising interpolating the identified closest matches to generate the retrieved one of the calibration data sets in the sequence of calibration data sets.

\* \* \* \* \*